United States Patent
Milnes

[11] 4,262,119
[45] Apr. 14, 1981

[54] TRIS-(POLYALKOXYLATED), ISOCYANURATES

[75] Inventor: Frank J. Milnes, Guilford, Conn.

[73] Assignee: Olin Corporation, New Haven, Conn.

[21] Appl. No.: 156,898

[22] Filed: Jun. 6, 1980

Related U.S. Application Data

[62] Division of Ser. No. 954,393, Oct. 25, 1978.

[51] Int. Cl.³ .................................. C07D 251/34
[52] U.S. Cl. .................................................. 544/221
[58] Field of Search ........................................ 544/221

[56] References Cited

U.S. PATENT DOCUMENTS

| | | | |
|---|---|---|---|
| 2,977,360 | 3/1961 | Dixon et al. | 544/221 |
| 3,249,607 | 5/1966 | Taub et al. | 544/221 |
| 3,637,557 | 1/1972 | Little | 544/221 |
| 3,730,923 | 5/1973 | Formaini et al. | 544/221 |
| 3,741,966 | 6/1973 | Weedon et al. | 544/221 |
| 3,859,284 | 1/1975 | Formaini et al. | 544/221 |
| 3,870,716 | 3/1975 | Belsky et al. | 544/221 |

OTHER PUBLICATIONS

K. Fukui et al., *Chemical Abstracts*, vol. 63, entry 18087b (1965).

*Primary Examiner*—John M. Ford
*Attorney, Agent, or Firm*—William A. Simons; Thomas P. O'Day

[57] ABSTRACT

Novel tris-(polyalkoxylated) isocyanurate compounds are described having the formula:

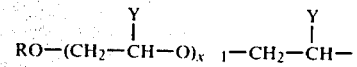

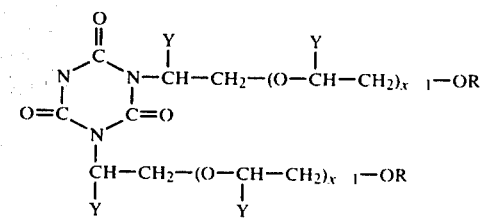

wherein X is an integer from 2–10; Y is either a hydrogen or methyl group; and R is an alkyl group having from 1–4 carbon atoms. The use of these isocyanurate compounds as functional fluids, including hydraulic-type and heat transfer-type fluids, is also described. Such functional fluids have superior fire resistance properties.

7 Claims, No Drawings

TRIS-(POLYALKOXYLATED), ISOCYANURATES

This is a division, of application Ser. No. 954,393, filed Oct. 25, 1978.

BACKGROUND OF THE INVENTION

1. Field of the Invention

This invention relates to novel isocyanurate compounds and their use in functional fluid systems. More particularly, this invention relates to novel tris-(polyalkoxyalkoxyalkylated) isocyanurate compounds and their use in functional fluid systems.

2. Description of the Prior Art

Tris-(substituted) isocyanurate compounds (i.e., isocyanurate esters having the same substituents at each of three ring nitrogens) have been widely described in the literature. In particular, ethylene oxide adducts of isocyanurates, and mixtures thereof, as well as certain carboxylic acid esters of the resulting polyols, have been described. For example, see U.S. Pat. No. 3,637,557, which issued to E. D. Little on Jan. 25, 1972. The described isocyanurate compounds have been found to be useful in a variety of applications, including functional fluid applications.

Moreover, the prior art generally teaches that alkoxy alkyl chlorides may be reacted with cyanuric acid in the presence of a base. See Col. 2, line 26 of U.S. Pat. No. 3,075,979. However, this teaching failed to recognize the possible utilization of such a reaction product as functional fluids. Furthermore, a literature article describes three specific tris-(mono-alkoxyalkylated) isocyanurate compounds, i.e., tris-($CH_3OCH_2CH_2$) isocyanurate, tris-($C_2H_5OCH_2CH_2$)-isocyanurate and tris-($C_4H_9OCH_2CH_2$) isocyanurate. See Bull. Chem. Soc. Japan, Volume 38 (10), pages 1586–1589 (1965). But such teachings do not describe or suggest the novel tris-(polyalkoxyalkylated) isocyanurate compounds of the present invention nor describe their use as fire resistant functional fluids.

BRIEF SUMMARY OF THE INVENTION

The present invention is directed at tris-(polyalkoxyalkylated) isocyanurate compounds of the formula:

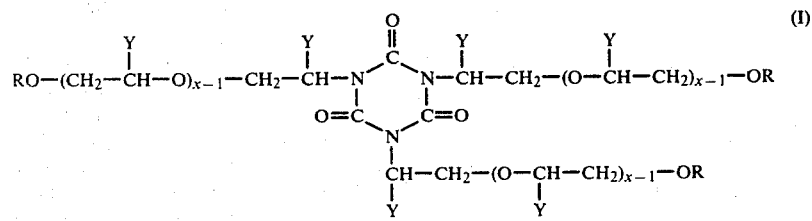

wherein x is an integer from 2–10; Y is either a hydrogen or methyl group; and R is a lower alkyl group having from 1–4 carbon atoms.

This invention is also directed to the use of these isocyanurate compounds as functional fluids, including hydraulic-type and heat transfer-type functional fluids. Such functional fluids have superior fire resistance properties.

DETAILED DESCRIPTION

The compounds of Formula I may be prepared by first reacting one or more polyglycol monoalkyl ethers with a chlorinating agent such as thionyl chloride to produce the corresponding mono-chloro compounds. This reaction is represented by the following Equation A:

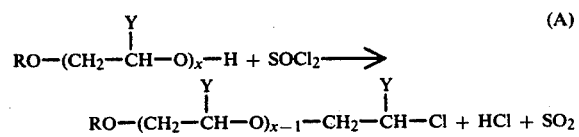

where x can vary from 2 to 10, preferably 2 to 5; Y can be hydrogen or methyl, preferably hydrogen; and R is lower alkyl having 1–4 carbon atoms, preferably a methyl group.

These mono-chloro compounds may be next reacted with trisodium cyanurate to form the instant compounds. This latter reaction is represented by Equation B:

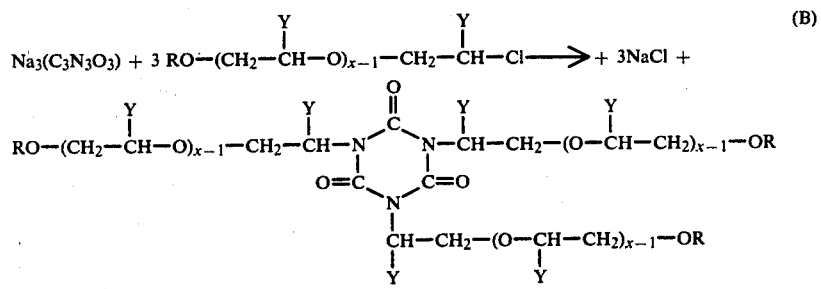

One of the unexpected characteristics of the compounds of the present invention, as seen in Table I, below, is an increase in fire resistance with increasing alkylene oxide content in the N-substituents. This is particularly unexpected because alkylene oxide compounds, i.e., ethylene oxide and propylene oxide, by themselves are highly flammable.

In the reaction illustrated by Equation A, polyglycol monoalkyl ethers are employed as a starting material. These polyglycol ethers are commercially available from several sources. For example, polyglycol ethers identified by the POLY-SOLV ® trademark and sold by the Olin Corporation are one suitable source. It is intended that the present invention may employ both substantially pure polyglycol ethers and mixtures thereof. Preferably, the polyglycol portion of these compounds has from 2 to 5 glycol groups, represented by having x in Equation A equal from 2-5. Also, monoalkyl portion of this compound is preferably a methyl group. Specific preferred embodiments include diethylene glycol monomethyl ether, triethylene glycol monomethyl ether, tetraethylene glycol monomethyl ether and mixtures thereof.

Thionyl chloride ($SOCl_2$) is employed as the chlorinating agent in Equation A. This compound is a preferred chlorinating agent because of its relatively low cost and the ease of its reacting with the polyglycol ethers. However, other conventional chlorinating agents such as $PCl_3$, $PCl_5$ or $POCl_3$ may be alternatively employed, if desired.

This chlorination reaction illustrated by Equation A is a well known reaction and may be carried out in any conventional manner. See Chemical Abstracts Vol. 58, 450a, (1963), and Journal of American Chemical Society, Vol. 63, page 2279 et seq. (1941). For example, the chlorinating agent $SOCl_2$ may be added to the polyglycol monoalkyl ether in any standard reaction apparatus, preferably one with a gas scrubber to remove any gases generated during and after the reaction. Preferably, a 10-40% molar excess of the $SOCl_2$ over the polyglycol ether is empolyed to ensure the latter's substantially complete reaction. Furthermore, the reaction is preferably carried out at about ambient temperature (i.e., from about 0° C. to about 30° C.) and at atmospheric pressure. Usually, the period for adding the $SOCl_2$ to the polyglycol ether is about 60 minutes, followed by from about 15 minutes to 300 minutes of heating time in order to obtain a suitable yield of the desired monochloro product. Any inert solvent may be employed, although, preferably, no solvent is needed. Any conventional recovery system for isolating the desired chloropolyglycol monoalkyl ether may be employed. Usually, all of normal by-products (i.e., HCl and $SO_2$) are gaseous in nature and will bubble off during reaction, leaving the desired product in the reactor. If a substantially pure product is desired, purification by distillation may be employed.

The reaction of the chloropolyglycol-monoalkyl ether and trisodium cyanurate, as illustrated above by Equation (B), may be carried out in the reaction apparatus employed for the chlorination reaction or in separate conventional reaction apparatus. Ths trisodium cyanurate may be added to the product of the prior reaction, or vice versa. Moreover, chemical equivalents to the trisodium cyanurate may be employed, if desired, to make the novel tris-(polyalkoxyalkylated-isocyanurate compounds of the present invention. Trisodium cyanurate is commercially available, or may be easily made by the neutralization of cyanuric acid by well-known methods.

This isocyanurate reaction illustrated by Equation (B) normally employs a chloropolyglycol monoalkyl ether to trisodium cyanurate molar ratio in the range of about 2.5:1 to about 5:1, more preferably about 3:1 to ensure good yields of the compounds of the present invention. The reaction temperatures of this reaction usually are in the range of from about 100° C. to about 200° C., more preferably in the range of 120° C. to about 150° C. Furthermore, the reaction is most preferably carried out at atmospheric pressure, although pressure in the range from 0.5 atm. to 100 atm. may be used if desired. Such higher pressures are employed if solvent is a lower boiling solvent. Preferably, the reaction is carried out in the presence of an aprotic polar solvent. Examples of such suitable solvents include N,N-dimethylformamide (DMF), dimethylsulfoxide, hexamethylphosphorylamide and the like. DMF is the most preferred solvent. Preferably, such solvents are employed in a range from about 2:1 to about 10:1, more preferably, about 4:1 to about 6:1, molar excess over the trisodium cyanurate. The time of the reaction usually includes about 30-120 minutes for adding the reactants together, preferably followed by a heating period from about 120 minutes to about 1200 minutes, more preferably, from about 600 minutes to 720 minutes.

The products of the present invention can be recovered from the reaction mixture by any conventional method. Preferably, the by-product NaCl is first removed from the reaction mixture by conventional filtration techniques. Next, the solvent is then preferably removed by vacuum stripping. The remaining reaction mixture may be distilled by conventional methods such as molecular distillation to obtain a very pure product, if desired.

Of course, the novel tris-(N-polyalkoxyalkylated)-isocyanurate compounds of the present invention may be made by other methods and the present invention is not intended to be limited to any specific method of making these compounds.

The isocyanurate compounds of the present invention have been found to be particularly useful in functional fluid systems. The functional fluid systems to which the present invention is directed includes hyraulic-type functional fluid systems and heat transfer-type functional fluid systems.

The hydraulic-type fluid systems include any system wherein a mechanical effort is converted to pressure at a first location, the pressure is transmitted from this location to a second location via a hydraulic fluid, and the pressure is converted to a second mechanical effort at the second location. Thus, the hydraulic systems contemplated by the present invention include hydraulic brake systems, hydraulic steering mechanisms, hydraulic transmissions, hydraulic jacks and hydraulic lifts, especially those that require a high degree of fire resistance. Included among these are the hydraulic systems used in heavy equipment and transportion vehicles including a highway and construction equipment, railways, planes and aquatic vehicles.

The heat transfer-type fluid systems include the hydraulic systems described above wherein heat is dissipated by the hydraulic fluid and include many other systems as well. In general, the present invention contemplates heat transfer systems wherein heat is passed from a first heat conductor at a first location to a heat transfer fluid, the heat is transmitted from the first location to a second location via the heat transfer fluid, and the heat is passed from the heat transfer fluid to a second conductor at the second location. Thus, the heat transfer systems of the present invention include heat dissipation systems, fluidic heating systems, e.g., radiator-type circulating fluid heating systems, heating exchange systems such as gas-liquid and liquid-liquid concurrent and countercurrent tubular heat exchangers as are used, for example, in the chemical process industries, cooling systems for nuclear reactors, radiator-type cooling systems, and any other temperature gradient systems in which a closed or sealed fluid heat transfer medium is used.

In the functional fluid systems of the present invention, the compounds of Formula I above are used in an effective amount. Thus, by an effective amount of these compounds is meant the compound product without additional fluid components as well as fluids containing additional fluid components. In one embodiment, the compounds of Formula I may be employed without additives or diluents. Alternatively, these compounds may comprise the base component of a functional fluid or may constitute a minor component, e.g., an additive in a functional fluid containing a different base component. In general, an effective amount may be any amount which will produce the desired fluid characteristics for a given system. Therefore, as little as 5% or less of one or more of the compounds of Formula I may be used or as much as about 100% of the compounds may be used, percentages by weight. Preferably about 20% to about 95% of the functional fluid may be one or more of the compounds of Formula I; more preferably, about 45% to about 90% of the fluid may comprise one or more compounds of Formula I.

Various diluents, inhibitors and other additives are well known in the functional fluid art and these may optionally be added to the functional fluids used in the systems of the present invention, if desired. For example, a diluent component may be one or more glycol monoethers or diethers or formals of the formula:

$$R_1[O-R_2]_xOR_3 \qquad (II)$$

wherein $R_1$ is a lower alkyl of 1 to 4 carbon atoms; $R_2$ is alkylene of 1 to 4 carbon atoms; $R_3$ is hydrogen or an alkyl of 1 to 4 carbon atoms; and x is an integer from 2 to 4. The $R_1$, $R_2$ and $R_3$ groups may be straight chained or branched and the alkylene oxide group $OR_2$ in the above formula may comprise mixtures of alkylene oxides. Also included among the possible diluents are one or more glycols, such as the alkylene glycols, having the formula:

$$HO(R_4O)_yH \qquad (III)$$

wherein $R_4$ is an alkylene of 2 to 3 carbon atoms and y is an integer from 1 to 5.

Illustrative of the above-described diluents are the following: diethylene glycol monoethyl ether, diethylene glycol monobutyl ether, triethylene glycol monomethyl ether, triethylene glycol monoethyl ether, tetraethylene glycol monomethyl ether, ethylene glycol, propylene glycol, diethylene glycol and tetraethylene glycol and the various alkyl ethers of the above glycols. Various other diluents and mixtures thereof; for example, water, may also be used.

Generally, the particular amount of diluents which is used is not critical and widely varying amounts may be used. More particularly, the diluent components may constitute from 0 up to about 80% by weight of the fluid and preferably from about 20 to about 60%.

Various additives may be added to the fluids used in the systems of this invention to control or modify various chemical and physical properties. Among the various types of additives which can be added to the fluids are included inhibitors for pH and corrosion control, antioxidants, rust inhibitors, viscosity index improvers, pour point depressants, lubraicating additives, antifoamants, stabilizers, vapor phase corrosion inhibitors, rubber swelling adjusters, demulsifiers, dyes and odor suppressants. Generally, the total amount of additives which may be incorporated into the fluid composition will vary between about 0 to about 20%, e.g., from about 0.1 to 8% and more specifically from about 0.2 to about 5% by weight based on the total weight of the fluid composition.

For example, alkaline inhibitors for pH and corrosion control may optionally be employed in an amount sufficient to maintain alkaline conditions in the fluid compositions, e.g., at an apparent pH value of from about 7 to about 11.5, if desired. These inhibitors may generally be added in an amount of from about 0 to about 8% by weight based on the total weight of fluid compositions, e.g., from about 0.5 to about 6%. Useful alkaline inhibitors include, for example, alkali metal salts of higher fatty acids such as potassium oleate, the potassium soap of rosin or tall oil fatty acids, amines such as morpholine and ethanolamine and amine salts such as mono- or dibutyl ammonium borates.

An antioxidant may optionally be used, if desired. Typical antioxidants include 2,2-di(4-hydroxyphenyl) propane, phenothiazine, amines such as phenylalphanaphthylamine and hindered phenols such as dibutyl cresol. Generally, the amount of antioxidant used will vary from 0 to about 3% by weight, e.g., from about 0.001 to about 2% by weight based on the total weight of the fluid composition.

Additionally, other additives, if desired, may be incorporated into the fluid composition. For example, corrosion inhibitors such as butynediol and rubber swelling adjusters such as dodecyl benzene may be used.

The above-noted inhibitors and additives are merely exemplary and are not intended as an exclusive listing of the many well-known materials which can be added to fluid compositions to obtain various desired properties. Other illustrations of additives and diluents which may be used can be found in U.S. Pat. No. 3,377,288, and in *Introduction to Hydraulic Fluids* by Roger E. Hatton, Reinhold Publishing Corp. (1962).

The following examples depict various embodiments of the present invention; they are intended to be illustrative and not limiting in nature. All parts and percentages are by weight unless otherwise specifield.

EXAMPLE 1

Formation of $(C_3N_3O_3)[(C_2H_4O)_3 CH_3]_3$

A one liter three neck flask is equipped with a stirrer, reflux condenser and an adapter, carrying a dropping funnel and a thermometer. Provisions are made to blanket the system with nitrogen during the reaction.

The flask is heated by a mantle, which in turn is connected to a temperature controller.

The reactor is charged with 87.8 g trisodium cyanurate $Na_3(C_3N_3O_3)$ (0.45 moles) and slurried with 300 ml N,N-dimethylformamide (DMF). The dropping funnel is charged with 249.1 g monochlorotriethyleneglycolmonomethyleter, $[Cl(C_2H_4O)_3]$ 99.0% purity (1.35 moles).

The reaction flask is purged with nitrogen and the thermostat set for 64° C. When this temperature is reached, the addition of the chloride is started and maintained at such a rate that about 1.5 hours are required for the addition. During this time the pot temperature is allowed to rise to 80° C. by periodic readjustment of the temperature controller. After the addition is completed, the pot temperature is set to 130° C. and maintained there for 12 hours, while the reactor is stirred.

The mixture is now cooled, filtered and the NaCl filter cake is washed twice with about 120 ml DMF each. Filtrate and these washers are combined.

To check for completion of the reaction, the NaCl filter cake is freed from adhering DMF by several diethyl ether washes and then vacuum dried and weighed. 80.5 g NaCl is obtained.

The filtrate is vacuum stripped to remove the DMF. The remaining crude turbid product is again filtered to yield 219.9 g of clear product.

Molecular distillation at between $10^{-3}$ and $5 \times 10^{-4}$ mm Hg gives 8.5 g forecut, distilling at an evaporator temperature of 100° C.

At a temperature of 225° C., 155.4 g product is recovered leaving 43.8 g undistilled residue.

The distilled main cut represents a 60.8% yield of product based on $Na_3(C_3N_3O_3)$ charged. An analysis of some of the product's physical characteristics is shown in Table I, below.

EXAMPLE 2

Formation of $(C_3N_3O_3)[(C_2H_4O)_4CH_3]_3$

Using the experimental set up as in Example 1, 107.3 g $Na_3C_3N_3O_3$ (0.55 moles) in 400 ml DMF, reacted with 391.7 g $Cl(C_2H_4O)_4CH_3$ (95.5% purity, 1.65 moles) gives after work up, 333.4 g crude product.

The molecular distillation, again carried out between $10^{-3}$ and $5 \times 10^{-4}$ mm Hg, gave a 53.7 g distillate forecut at 150° C. and a 225.5 g main cut distillate and 44.1 g residue at 275° C.

The main cut product was obtained in 58.2% yield based on $Na_3C_3N_3O_3$ charged. An analysis of some of the product's physical characteristics is shown in Table I, below.

EXAMPLE 3

Formation of $(C_3H_3O_3)[(C_2H_4O)_2CH_3]_3$

With the experimental set up as in Example 1, 87.8 g $Na_3C_3N_3O_3$(0.45 mole) in 350 ml DMF was reacted with 214.7 g $Cl(C_2H_4O)_2CH_3$(91.5% purity, 1.41 moles) resulting in 232.9 g vacuum stripped product.

Repeating this reaction with the same amounts of reactants at 80° C. instead of 135° C. gave a vacuum stripped product weighting only 96.3 g.

A molecular distillation was carried out on a 317.0 g combined sample of these two products. Distillation at 140° C. and $5 \times 10^{-4}$ mm Hg gave a 56.4 g forecut distillate. The remaining residual was first filtered through a filter aid to remove a slight turbidity and then distilled at 205° C. and $5 \times 10^{-2}$ mm in the molecular distillation system. This yielded a 145.4 g main cut product and 16.9 g residue.

The combined yield is 37.9% by weight based on $Na_3C_3N_3O_3$ charged. An analysis of the product's physical characteristics is shown in Table I, below.

COMPARISON 1

Formation of $(C_3N_3O_3)(C_2H_4OC_4H_9)_3$

Using the experimental set up as in Example 1, 136.5 g $Na_3C_3N_3O_3$(0.7 mole) in 500 DMF was reacted with 297.7 g $ClC_2H_4OC_4H_9$ (2.136 moles, 98.8% by weight purity) to give 153.2 g vacuum stripped product.

Molecular distillation at 150° C., $10^{-3}$ mm Hg followed at 195° C., $5 \times 10^{-2}$ mm Hg yielded a combined distillate main product weighing 142.8 g. An analysis of this product's physical characteristics is shown in Table I, below.

TABLE I

PHYSICAL AND FLAMMABILITY PROPERTIES OF CYANURATE FLUIDS

| Example | Compounds | Visc.[1] 100° F. | Visc.[1] 210° F. | Visc.[2] Index | Flash[3] Point (°F.) | Pour[4] Point (°F.) |
|---|---|---|---|---|---|---|
| C1 | $(C_3N_3O_3)(C_2H_4OC_4H_9)_3$ | 36.75 | 4.83 | 58 | 370 | −44 |
| 3 | $(C_3N_3O)[(C_2H_4O)_2CH_3]_3$ | 58.14 | 6.57 | 85 | 345 | −27 |
| 1 | $(C_3N_3O)[(C_2H_4O)_3CH_3]_3$ | 45.08 | 6.58 | 107 | 380 | −38 |
| 2 | $(C_3N_3O)[(C_2H_4O)_4CH_3]_3$ | 43.58 | 7.18 | 138 | 390 | −44 |

| 4 Ball[5] Wear (mm) | Wick[6] Test (Cycles) | Spray[7] Mist. Flam. | Autoignition[8] Temperature |
|---|---|---|---|
| 0.78 | 10 | Fire at torch | 709° F. |
| 1.17 | 16 | Fire at torch | 721° F. |
| 1.02 | 16 | Fire at torch | 730° F. |
| 0.71 | 23 | No fire | 736° F. |

[1]Viscosity is measured according to test method given in ANSI/ASTM D445-74 - Kinematic Viscosity of Transparent and Opaque Liquids.
[2]Viscosity Index is calculated according to the method given in ANSI/ASTM D2270-77 - Calculating Viscosity Index from Kinematic Viscosity at 100° F. and 210° F. (Appendix 2).
[3]Flash Point is measured generally according to test method ANSI/ASTM D3243-77 - Standard Test Method for Flash Point of Aviation Turbine Fuels by Setaflash Closed Tester (except employed 4 ml of sample in a high temperature Setaflash instrument).
[4]Pour Point is measured according to test method ANSI/ASTM D97-66(1971) - Standard Test Method for Pour Point of Petroleum Oils.
[5]4 Ball Wear is measured according to test method ANSI/ASTM D2266-67(1977) - Standard Test Method for Wear Prevention Characteristics of Lubricating Grease (Four-Ball Method), employing conditions of 1 hour, 167° F., 1200 rpm and 40 kg load.
[6]Wick Test is determined according to U.S. Bureau of Mines Schedule 30.
[7]Spray Mist Flammability is determined according to ANSI/ASTM D3119-75 - Standard Test Method for Mist Spray Flammability of Hydraulic Fluids.
[8]Autoignition Temperature is determined according to ANSI/ASTM D2155-66(1976) - Standard Test Method for Autoignition Temperature of Liquid Petroleum Products.

For all tests except Viscosity and Pour point test, one part by weight anti-oxidant (phenyl-alpha-naphthylamine) was added to 100 parts of each product.

What is claimed is:

1. Tris-(polyalkoxyalkylated)-isocyanurate compounds of for formula:

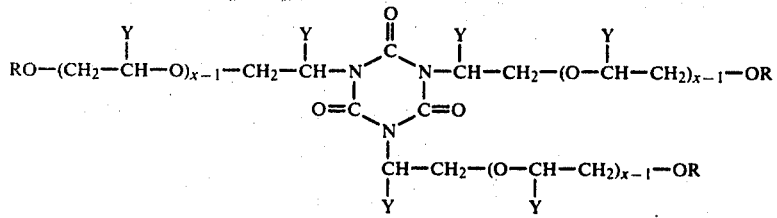

wherein x is an integer from 2-10; Y is either hydrogen or methyl group; and R is a lower alkyl group having from 1-4 carbon atoms.

2. The compound of claim 1, wherein x is from 3 to 5.
3. The compound of claim 1, wherein Y is hydrogen.
4. The compound of claim 1, wherein R is a methyl group.
5. The compound of claim 1, having the formula:

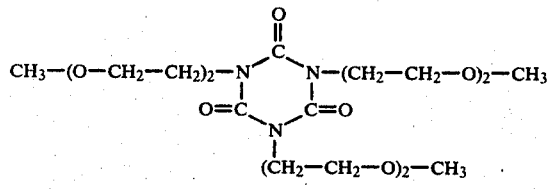

6. The compound of claim 1, having the formula:

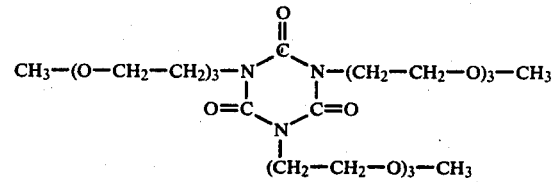

7. The compound of claim 1, having the formula:

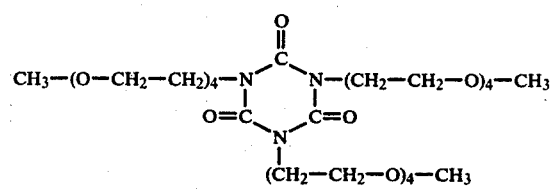

* * * * *

UNITED STATES PATENT AND TRADEMARK OFFICE
CERTIFICATE OF CORRECTION

PATENT NO. : 4,262,119

DATED : April 14, 1981

INVENTOR(S) : Frank J. Milnes, Robert J. Bucko, David F. Gavin

It is certified that error appears in the above-identified patent and that said Letters Patent are hereby corrected as shown below:

On the Title Page under "United States Patent [19]" after "Milnes" please insert --et al.--.

On the Title Page after "[54]" delete "TRIS-(POLY-ALKOXYLATED), ISOCYANURATES" and insert --TRIS-(POLY-ALKOXYALKYLATED) ISOCYANURATES On the Title Page after "[75]" delete "Inventor: Frank J. Milnes, Guilford, Conn." and insert
--Inventors: Frank J. Milnes, Guilford, Conn.
Robert J. Bucko, Hamden, Conn.
David F. Gavin, Cheshire, Conn.--

On the Title Page, on line 1 of the ABSTRACT after "Novel" delete "tris-(polyalkoxylated)" and insert --tris-(polyalkoxyalkylated)--.

On the Title Page, delete the following formula:

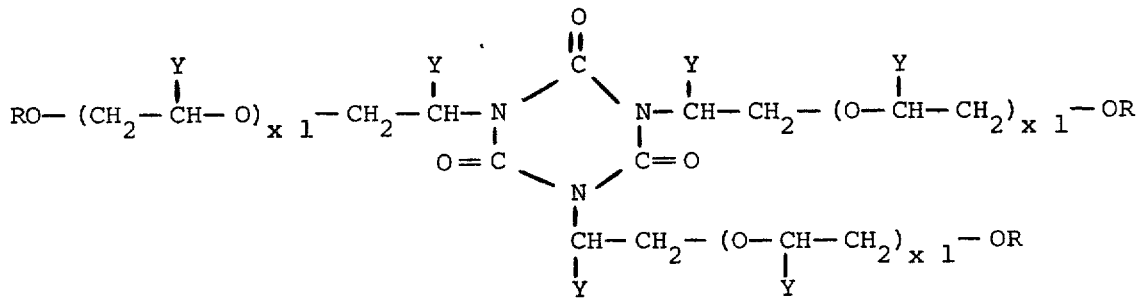

and insert the following formula:

UNITED STATES PATENT AND TRADEMARK OFFICE
CERTIFICATE OF CORRECTION

PATENT NO. : 4,262,119
DATED : April 14, 1981
INVENTOR(S) : Frank J. Milnes, Robert J. Bucko, David F. Gavin It is certified that error appears in the above-identified patent and that said Letters Patent are hereby corrected as shown below:

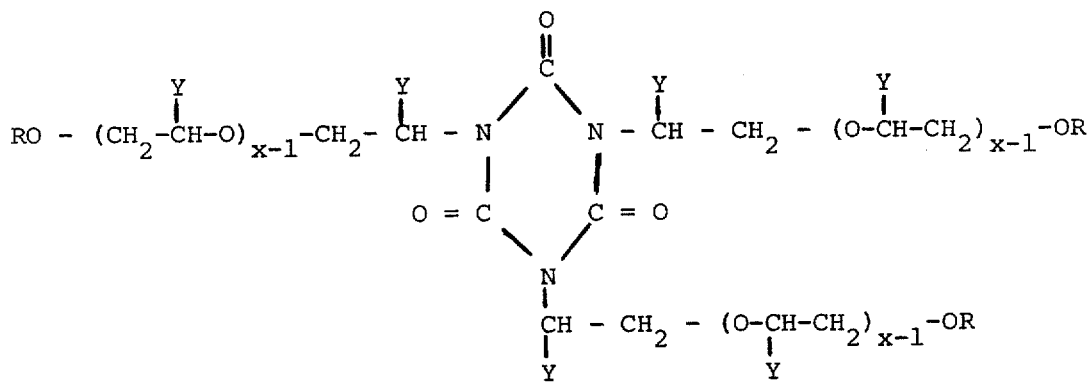

In Column 1 in the title, delete "TRIS-(POLYALKOXY-LATED), ISOCYANURATES" and insert --TRIS-(POLYALKOXY-ALKYLATED) ISOCYANURATES--.

In Column 1, lines 11 and 12 delete "tris-(polyalkoxy-alkoxyalkylated)" and insert --tris-(polyalkoxyalkylated)--.

In Column 3, line 49, delete "Ths" and insert --The--.

In Column 3, line 53, after "tris-(polyalkoxy-alkylated" and before "-isocyanurate" insert --)--.

In Column 4, line 38, before "location" (first occurrence) insert --first--.

In Column 5, line 63, delete "lubraicating" and insert --lubricating--.

UNITED STATES PATENT AND TRADEMARK OFFICE
CERTIFICATE OF CORRECTION

PATENT NO. : 4,262,119

DATED : April 14, 1981

INVENTOR(S) : Frank J. Milnes, Robert J. Bucko, David F. Gavin

It is certified that error appears in the above-identified patent and that said Letters Patent are hereby corrected as shown below:

In Column 6, line 42 (last line of last paragraph before Example 1) delete "specifield." and insert --specified.--

In Column 6, lines 56 and 57, delete "monochlorotriethyleneglycolmonomethyleter, [Cl(C$_2$H$_4$O)$_3$]" and insert --monochlorotriethyleneglycolmonomethylether, [Cl(C$_2$H$_4$O)$_3$CH$_3$]--.

In Column 8, line 21, after "500" and before "DMF" insert --ml--.

In Column 8, Claim 1, line 68, after "of" delete "for" and insert --the--.

Signed and Sealed this

Twenty-third Day of March 1982

[SEAL]

Attest:

GERALD J. MOSSINGHOFF

Attesting Officer

Commissioner of Patents and Trademarks